United States Patent [19]

Kim et al.

[11] Patent Number: 5,281,589
[45] Date of Patent: Jan. 25, 1994

[54] 3-FUSED PYRIDINIUMMETHYL CEPHALOSPORINS

[75] Inventors: Choong S. Kim; Seung H. An; Sung K. Cho; Yang S. Ahn; Kyoung E. Choi, all of Seoul; Je H. Kim; Rok L. Yun, both of Kyonggi-do; Sung Y. Park, Seoul; Yeo H. Yoon, Seoul; Chun S. Lyu, Seoul; Koun H. Lee, Seoul, all of Rep. of Korea

[73] Assignee: Cheil Foods & Chemicals, Inc., Seoul, Rep. of Korea

[21] Appl. No.: 896,667

[22] Filed: Jun. 10, 1992

[30] Foreign Application Priority Data

Jun. 15, 1991 [KR] Rep. of Korea ............... 91-9930[U]
Feb. 12, 1992 [KR] Rep. of Korea ............... 92-2067[U]

[51] Int. Cl.$^5$ ................. C07D 501/38; A61K 31/545
[52] U.S. Cl. ..................................... 514/206; 540/225
[58] Field of Search ............... 540/222, 225; 514/202, 514/205, 206

[56] References Cited

U.S. PATENT DOCUMENTS

| 4,098,888 | 7/1978 | Ochiai et al. | 424/246 |
| 4,152,432 | 5/1979 | Heymes et al. | 424/246 |
| 4,258,041 | 3/1981 | O'Callaghan et al. | 424/246 |
| 4,748,172 | 5/1988 | Katner | 514/206 |

FOREIGN PATENT DOCUMENTS

0164944A1 12/1985 European Pat. Off.

Primary Examiner—Nicholas S. Rizzo
Attorney, Agent, or Firm—Burns, Doane, Swecker & Mathis

[57] ABSTRACT

Novel semi-synthetic cephalosporin derivatives having a fused pyridiniummethyl at 3-position of the cephem nucleus, pharmaceutically acceptable salts, physiologically hydrolizable esters or solvates thereof are disclosed. Also disclosed is a process for preparing the cephalosporin derivatives which comprises introducing a fused pyridiniummethyl substituent at 3-position of 7-β-[(Z)-2-(2-aminothiazol-4-yl)-2-methoxyiminoacetamido]-3-cephem-carboxylic acid derivatives. The compounds of the present invention show potent antibacterial activities and a broad spectrum against both gram-positive and gram-negative bacteria.

10 Claims, No Drawings

3-FUSED PYRIDINIUMMETHYL CEPHALOSPORINS

BACKGROUND OF THE INVENTION

1. Field of the Invention

The present invention relates to novel cephalosporin derivatives, and a pharmaceutically acceptable salt, physiologically hydrolyzable ester and solvate thereof. This invention also relates to a process for their preparation, a use thereof as antibiotics, and a pharmaceutical composition containing the same derivatives as an active ingredient.

2. Description of the Prior Art

A number of cephalosporin compounds have been synthesized in which the cephem nucleus has a quarternary ammonium methyl at its 3-position and various acylamino groups at its 7-position. These compounds exhibit selective toxicity against bacteria only and present no substantial effects against animal cells. They have been widely used for the treatment of infectious diseases caused by bacteria as antibiotics having no substantial side effects. Thus, they are highly useful as drugs.

In recent years, an extensive investigation has been made to develop novel cephalosporin derivatives which have more potent antibacterial activities and a broad antibacterial spectrum, especially coupled with activities against cephalosporin resistant bacteria.

As a result, a number of cephalosporin derivatives have been developed which have a 2-(2-aminothiazol-4-yl)-2-substituted oxyiminoacetamido group as a side chain at 7-position and a fused pyridiniummethyl substituted at 3-position of the cephem nucleus. As prior art references which disclose such derivatives, U.S. Pat. No. 4,152,432 to Heymes et al.; U.S. Pat. No. 4,098,888 to Ochiai et al.; U.S. Pat. No. 4,258,041 to O'Callaghan; U.S. Pat. No. 4,748,172 to Katner; European Patent No. 0,318,552 to Katner; European Patent No. 0,164,944 to Bradbury; and European Patent No. 0,300,664 to Jung may be mentioned.

The present invention has been accomplished as an advanced improvement as compared with such investigation.

Thus, the object of the invention is to provide novel cephalosporin derivatives having strong activities and a broad antibacterial spectrum against both gram-positive and gram-negative bacteria, as well as excellent stability against β-lactamase.

DISCLOSURE OF THE INVENTION

The present invention provides novel cephalosporin derivatives having the formula:

(I)

wherein $R_1$ is hydrogen, or a lower alkyl, $C_3$-$C_4$ alkenyl, $C_3$-$C_4$ alkynyl or cycloalkylalkyl group, a fluoro-substituted lower alkyl group represented by the formula: $-(CH_2)_xF$ in which x is an integer of 1 to 3, or a carboxy-substituted alkyl group represented by the formula:

$$-\underset{R'''}{\overset{R''}{\underset{|}{\overset{|}{C}}}}-(CH_2)_y-COR'$$

wherein R' is a hydroxy, amino or $C_1$-$C_4$ alkoxy group; R" and R"', which may be the same or different, represent hydrogen or a $C_1$-$C_3$ alkyl group, or R" and R"' together with the carbon atom to which they are attached may form a $C_3$-$C_7$ carbocylic ring; and y is an integer of 0 to 3;

$R_2$ and $R_3$, which may be the same or different, represent hydrogen, or a lower alkyl, amino, carboxy-substituted lower alkyl, hydroxy-substituted lower alkyl or $C_3$-$C_7$ cycloalkyl group;

n is an integer of 1 or 2; and the 2-oxo-heterocyclic moiety is fused with the pyridine ring to form a 2,3- or 3,4-fused ring substituent at 3-position of the cephem nucleus; or a pharmaceutically acceptable salt, physiologically hydrolyzable ester or solvate thereof.

The compounds of the present invention show strong activities against gram-positive bacteria such as Streptococcus, Staphylococcus, Methicillin resistant Staphylococcus, Corynebacterium, Bacillus, etc.; gram-negative bacteria such scherichia, Enterobacter, Klebsiella, Serratia, Salmonella, Proteus, Providensia, Morganella, Pseudomonas, etc.; and various drug resistant bacteria. Particularly preferred specific compounds according to the invention are as set forth below:

7-β-[(Z)-2-(2-aminothiazol-4-yl)-2-methoxyiminoacetamido]-3-[2,3(1H,4H)-dioxo-pyrazino[5,6-c]pyridiniummethyl]-3-cephem-4-carboxylate;

7-β-[(Z)-2-(2-aminothiazol-4-yl)-2-ethoxyiminoacetamido]-3-[2,3(1H,4H)-dioxo-pyrazino[5,6-c]pyridiniummethyl]-3-cephem-4-carboxylate;

7-β-[(Z)-2-aminothiazol-4-yl)-2-propynyloxyiminoacetamido]-3-[2,3(1H,4H)-dioxo-pyrazino[5,6-c]pyridiniummethyl]-3-cephem-4-carboxylate;

7-β-[(Z)-2-(2-aminothiazol-4-yl)-2-cyclopropylmethoxyiminoacetamido]-3-[2,3(1H,4H)-dioxo-pyrazino[5,6-c]-pyridiniummethyl]-3-cephem-4-carboxylate;

7-β-[(Z)-2-(2-aminothiazol-4-yl)-2-carboxymethoxyiminoacetamido]-3-[2,3(1H,4H)-dioxo-pyrazino[5,6-c]pyridiniummethyl]-3-cephem-4-carboxylate;

7-β-[(Z)-2-(2-aminothiazol-4-yl)-2-(2-carboxyprop-2-yl)-oxyiminoacetamido]-3-[2,3(1H,4H)-dioxo-pyrazino[5,6-c]-pyridiniummethyl]-3-cephem-4-carboxylate;

7-β-[(Z)-2-(2-aminothiazol-4-yl)-2-methoxyiminoacetamido]-3-[1-methyl-2,3(4H)-dioxo-pyrazino[5,6-c]-pyridiniummethyl]-3-cephem-4-carboxylate;

7-β-[(Z)-2-(2-aminothiazol-4-yl)-2-methoxyiminoacetamido]-3-[1-ethyl-2,3(4H)-dioxo-pyrazino[5,6-c]-pyridimiummethyl]-3-cephem-4-carboxylate;

7-β-[(Z)-2-(2-aminothiazol-4-yl)-2-methoxyiminoacetamido]-3-[1-cyclopropyl-2,3(4H)-dioxo-pyrazino[5,6-c]-pyridiniummethyl]-3-cephem-4-carboxylate;

7-β-[(Z)-2-(2-aminothiazol-4-yl)-2-(2-carboxyprop-2-yl)-oxyiminoacetamido]-3-[1-methyl-2,3(4H)-dioxopyrazino-[5,6-c]pyridiniummethyl]-3-cephem-4-carboxylate;

7-β-[(Z)-2-(2-aminothiazol-4-yl)-2-(2-carboxyprop-2-yl)-oxyiminoacetamido]-3-[1-ethyl-2,3(4H)-dioxo-pyrazino-[5,6-c]pyridiniummethyl]-3-cephem-4-carboxylate;

7-β-[(Z)-2-(2-aminothiazol-4-yl)-2-(2-carboxyprop-2-yl)-oxyiminoacetamido]-3-[1-cyclopropyl-2,3(4H)-dioxopyrazino[5,6-c]pyridiniummethyl]-3-cephem-4-carboxylate;

7-β-[(Z)-2-(2-aminothiazol-4-yl)-2-methoxyiminoacetamido]-3-[4-methyl-2,3(1H)-dioxo-pyrazino[5,6-c]-pyridiniummethyl]-3-cephem-4-carboxylate;

7-β-[(Z)-2-(aminothiazol-4-yl)-2-fluoromethoxyiminoacetamido]-3-[2,3(1H,4H)-dioxo-pyrazino[5,6-c]pyridiniummethyl]-3-cephem-4-carboxylate;

7-β-[(Z)-2-(2-aminothiazol-4-yl)-2-methoxyiminoacetamido]-3-[2(1H,3H)-oxo-imidazo[4,5-c]pyridiniummethyl]-3-cephem-4-carboxylate;

7-β-[(Z)-2-(2-aminothiazol-4-yl)-2-methoxyiminoacetamido]-3-[1-methyl-2(3H)-oxo-imidazo[4,5-c]pyridiniummethyl]-3-cephem-4-carboxylate;

7-β-[(Z)-2-(2-aminothiazol-4-yl)-2-methoxyiminoacetamido]-3-[1-amino-2(3H)-oxo-imidazo[4,5-c]pyridiniummethyl]-3-cephem-4-carboxylate;

7-β-[(Z)-2-(2-aminothiazol-4-yl)-2-methoxyiminoacetamido]-3-[1-(2-hydroxyethyl)-2(3H)-oxo-imidazo[4,5-c]-pyridiniummethyl]-3-cephem-4-carboxylate;

7-β-[(Z)-2-(2-aminothiazol-4-yl)-2-methoxyiminoacetamido]-3-[2(1H,3H)-oxo-imidazo[4,5-b]pyridiniummethyl]-3-cephem-4-carboxylate;

7-β-[(Z)-2-(2-aminothiazol-4-yl)-2-fluoromethoxyimino-acetamido]-3-[2(1H,3H)-oxo-imidazo[4,5-c]pyridiniummethyl]-3-cephem-4-carboxylate;

7-β-[(Z)-2-(2-aminothiazol-4-yl)-2-fluoromethoxyiminoacetamido]-3-[1-methyl-2(3H)-oxo-imidazo[4,5-c]pyridiniummethyl]-3-cephem-4-carboxylate;

7-β-[(Z)-2-(2-aminothiazol-4-yl)-2-fluoromethoxyiminoacetamido]-3-[1-amino-2(3H)-oxo-imidazo[4,5-c]pyridiniummethyl]-3-cephem-4-carboxylate;

7-β-[(Z)-2-(2-aminothiazol-4-yl)-2-fluoromethoxyiminoacetamido]-3-[2(1H,3H)-oxo-imidazo[4,5-b]pyridiniummethyl]-3-cephem-4-carboxylate; and 7-β-[(Z)-2-(2-aminothiazol-4-yl)-2-carboxymethoxyiminoacetamido]-3-[2(1H,3H)-oxo-imidazo[4,5-c]pyridiniummethyl]-3-cephem-4-carboxylate.

The new cephalosporin compounds of the present invention may be in the form of either a syn- or anti-isomer, or a mixture thereof consisting of at least about 90 % of a syn- isomer and not more than 10 % of an anti-isomer.

Also, if $R_1$ is a carboxy-substituted alkyl group represented by the formula: —C(R")(R''')COOH wherein R" and R''' are different from each other, then the carbon atom to which R" and R''' are linked may be an asymmetrical center, resulting in diastereoisomers. Therefore, the present invention also includes such diastereoisomers of the cephalosporin derivatives of the formula (I) above, and mixtures thereof.

The compounds of the formula (I) may be converted to non-toxic salts thereof by conventional methods. Such non-toxic salts may be pharmaceutically acceptable salts of the compound of the formula (I). Included among the non-toxic salts are an inorganic salt, for example, a metal salt such as an alkali metal salt (e.g., sodium salt, potassium salt, etc.), an alkaline earth metal salt (e.g., calcium salt, magnesium salt, etc.), ammonium salt, and so forth; an organic salt, for example, an organic amine salt (e.g., trimethylamine salt, triethylamine salt, pyridine salt, procaine salt, picoline salt, decyclohexylamine salt, N,N-dibenzylethylenediamine salt, N-methyl glucamine salt, diethanolamine salt, triethanolamine salt, tris(hydroxymethylamino) methane salt, phenylethylbenzylamine salt, dibenzylethylenediamine salt, and so forth; an organic carboxylic or sulfonic acid salt (e.g., formate, acetate, maleate, tartrate, methanesulfonate, benzenesulfonate, toluene sulfonate, etc.); an inorganic acid salt (e.g., hydrochloride, hydrobromide, sulfate, phosphate, etc.); a salt with a basic or acidic amino acid (e.g., arginine, aspartic acid, glutamic acid, lysine, etc.); and the like.

The physiologically hydrolyzable esters of the compounds of the formula (I) may include, for example, indanyl, phthalidyl, methoxymethyl, pivaloyloxymethyl, glycyloxymethyl, phenylglycyloxymethyl or 5-methyl-2-oxo-1,3-dioxolan-4-yl esters, and other physiologically hydrolyzable esters which have been widely used in penicillin and cephalosporin antibiotics chemistry.

The present invention further provides a process for preparing the novel cephalosporin derivatives of the formula (I) comprising the steps of: reacting a compound of the formula:

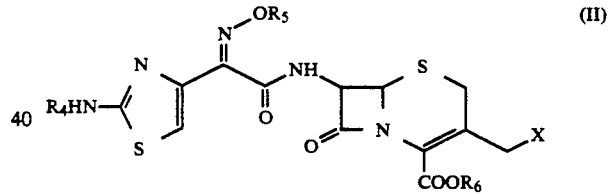

wherein $R_4$ is an amino protecting group;

$R_5$ is hydrogen, or a lower alkyl, $C_3$-$C_4$ alkenyl, $C_3$-$C_4$ alkynyl or cycloalkylalkyl group, a fluoro-substituted lower alkyl represented by the formula: —$(CH_2)_xF$, in which x is an integer of 1 to 3, or a carboxy-substituted alkyl group represented by the formula:

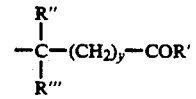

wherein R' is a hydroxy, amino or $C_1C_4$ alkoxy group; R" and R''' may be the same or different and represent hydrogen or a $C_1$-$C_3$ alkyl group, or R" and R''' together with the carbon atom to which they are attached may form a $C_3$-$C_7$ carbocylic ring; and y is an integer of 0 to 3;

$R_6$ is a carboxyl protecting group; and

X is a leaving group;

with a compound of the formula:

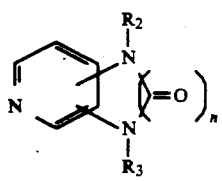

wherein $R_2$, $R_3$ and n have the same meaning as defined above and the 2-oxo-heterocyclic moiety is fused with the pyridine ring to form a 2,3- or 3,4-fused ring;
and then, if necessary, removing the amino protecting group and/or the carboxyl protecting group.

In the preparation of the objective compounds of the formula (I), the compound of the formula (II) is preferably used in an amount of from 1 to 2 equivalents based on 1 equivalent of the compound of the formula (III).

Now, the symbols and terms used in the specification will be explained.

The term "lower" as used hereinabove and elsewhere in this specification, for example, with reference to "lower alkyl," means those group having 1 to 6, preferably 1 to 4 carbon atoms.

The amino protecting group may include an acyl group; a substituted or unsubstituted aryl-lower alkyl group, for example, benzyl, diphenylmethyl, triphenylmethyl and 4-methoxybenzyl; a halo-lower alkyl group, for example, trichloromethyl and trichloroethyl; tetrahydropyranyl; a substituted phenylthio group; a substituted alkylidene group; a substituted aralkylidene group; and a substituted cycloalkylidine group as an amino protecting group may include, for example, a $C_1$–$C_6$ alkanoyl group such as formyl and acetyl; a $C_2$–$C_6$ alkoxy carbinyl group, for example, methoxycarbonyl and ethoxycarbonyl; a lower alkane sulfonyl group, for example, methane sulfonyl and ethane sulfonyl; or an aryl-lower alkoxy carbonyl group such as benzyloxycarbonyl. One to three substituents such as a halogen atom, or a hydroxy, cyano or nitro group can further be substituted for the acyl group. In addition, the amino protecting group may include the reaction products formed by a reaction of an amino group with silane, boron, or phosphorous compounds.

The carboxyl protecting group such as $R_6$ may include, for example, a lower alkyl group such as methyl and t-butyl; a lower alkenyl group such as vinyl and allyl; a lower alkoxy-lower alkyl group such as methoxymethyl; a lower alkylthio-lower alkyl group such as methylthiomethyl; a halo-lower alkyl group such as 2,2,2-trichloroethyl; a substituted or unsubstituted aralkyl group such as benzyl and p-nitrobenzyl; or a silyl group.

The amino or carboxyl protecting groups mentioned above may be readily removed under mild conditions by using a known method(See: T. W. Greene and P. G. M. Wuts. ]Protecting Groups in Organic Synthesis, 2nd Ed., John Wiley & Sons. 1991).

The leaving group, X, may include, for example, a halogen atom such as fluorine, chlorine, and iodine; a lower alkanoyloxy group such as acetoxy; a lower alkanesulfonyloxy group such as methanesulfonyloxy; an arenesulfonyloxy group such as p-toluenesulfonyloxy; an alkoxy carbonyloxy group; and the like.

BEST MODE FOR CARRYING OUT THE INVENTION

The displacement reaction of the compound of the formula (II) with the compound of the formula (III) is well performed when X is an acetoxy group or an iodine atom.

In an embodiment, a compound of the formula (II) in which X is an acetoxy group is first silylated with a silylating agent to protect the carboxy group at 4-position and the amino group of the substituent at 7-position. As the silylating agent, mono- or bis-trimethylsilylacetamide, N-methyl-N-(trimethylsilyl)acetamide, N,O-bis(trimethylsilyl)trifluoroacetamide, N-methyl-N-(trimethylsilyl)trifluoroacetamide (MSTFA) and hexamethyldisilazane (HMDS) may be used.

The silylated compound of the formula (II) is then reacted with trimethylsilyliodide (TMSI) at ambient temperature to form a compound of the formula (II) in which X is iodine. This reaction can be carried out in accordance with a known method, for example, as taught by U.S. Pat. No. 4,266,049 to Bonjouklian.

Separately, the fused pyridine of the formula (III) is silylated at room temperature in an aprotic organic solvent using the same silylating agent as mentioned above.

The resulting silylated 3-iodomethyl cephalosporin of the formula (II) is then reacted with the silylated fused pyridine of the formula (III) to give a silylated compound of the formula (I). Hydrolysis of the silyl groups provides a compound of the formula (I) according to the present invention.

The reaction for introducing the substituent of the formula (III) at 3-position of the compound of the formula (II) to prepare the compound of the formula (I) is carried out in the presence of an organic solvent such as an anhydrous aprotic solvent. As an appropriate organic solvent, there may be mentioned a nitrile solvent such as acetonitrile and propionitrile; an alkyl halide solvent such as chloroform, carbon tetrachloride and dichloromethane; an ether solvent such as tetrahydrofuran and dioxane; an amide solvent such as N,N-dimethyl formamide; an ester solvent such as ethylacetate and methylacetate; a ketone solvent such as acetone, methyl ethyl ketone and methyl isobutyl ketone; a sulfoxide solvent such as dimethylsulfoxide; and an aromatic carbohydrogen solvent such as benzene and toluene. This reaction may be carried out at 0° C. to 25° C.

In an alternative embodiment, the compounds of the formula (I) according to the invention are prepared directly from a 3-acetoxymethyl compound, for example, a compound of the formula (II) in which X is an acetoxy and $R_4$ is H.

This reaction is carried out in a conventional manner, for instance, in an aqueous medium, for example in an organic solvent in admixture with water. Addition of a small amount of an alkali iodide such as potassium iodide can enhance the rate of the reaction. This reaction is carried out at a temperature between about 35° C. and about 70° C. Useful water miscible organic solvents include acetone, acetonitrile, tetrahydrofuran, and dimethylacetamide.

However, it is preferred to use the former method, i.e., reacting a compound of the formula (II) in which X is iodine with a compound of the formula (III) in view of the reactivity and yields.

The amino or carboxyl protecting groups can be readily removed by a conventional deprotection method well known in cephalosporin antibiotics chemistry. For example, acid- or base-hydrolysis or reduction are generally applicable. For example, when the protecting group is an amido group, such compound is subjected to imino-halogenation and iminoetherification, followed by hydrolysis. Acid hydrolysis is preferably applicable to the removal of the groups such as tri(di)-phenylmethyl or alkoxycarbonyl. As a preferred acid for this purpose, there may be mentioned organic acids such as formic acid, trifluoroacetic acid and p-tolueneacetic acid; or an inorganic acid such as hydrochloric acid and the like.

During and after the preparation, a stabilizing agent can be used to stabilize reaction products and their intermediates. As a stabilizing agent, one or more salts selected from the group consisting of sodium iodide, potassium iodide, sodium bromide, potassium bromide and potassium thiocyanate can be mentioned.

The compounds of the formula (I) have the same stereochemistry as the known cephalosporin antibiotics. That is, the side chain at 7-position has a $\beta$-configuration (6R,7R), while the oxyimino group in the side chains may be in either a syn- or anti-form, or as a mixture thereof. Thus, the compounds of the present invention are prepared in either form by employing the 2-(heterocyclic)-2-oximinoacetic acid in the syn- or anti-form and coupling reagents. Instead, separation and purification of the compounds of the formula (I) can be performed by means of recrystallization, column chromatography, or ion exchange chromatography.

The present invention also provides a pharmaceutical composition comprising, as an active ingredient, one or more of the compounds of the formula (I) according to the present invention, a non-toxic salt, physiologically hydrolyzable ester or solvate thereof, in association with pharmaceutically acceptable carriers, excipients, or other additives.

The antibiotic compounds of the formula (I), as well as a non-toxic salt, physiologically hydrolyzable ester or solvate thereof may be formulated for administration, which may be presented in an unit dose form or in a multidose container. The formulation may be in various forms such as solutions, suspensions, or emulsions in oily or aqueous vehicles, which can contain conventional additives such as dispersing agents, suspending agents, stabilizing agents, and the like. In addition, the compounds of the present invention may be formulated into a dried powder that can be normally dissolved in an aqueous solution of sterile, pyrogen-free water, prior to use. The compounds of the present invention may also be formulated into a suppository containing conventional suppository bases such as cocoa and other glycerides.

PREFERRED EMBODIMENT OF THE INVENTION

The present invention will be described in greater detail by way of the following examples. The examples are presented for illustration purpose only and should not be construed as limiting the invention which is properly delineated in the claims.

PREPARATION 1

Preparation of
2,3(1H,4H)-dioxo-pyrazino[5,6-c]-pyridine

To a solution of 4 g of 3,4-diaminopyridine in 120 ml of methanol, 4.36 g of sodium methoxide was added, and the mixture was stirred at room temperature for 30 minutes. A solution of 4.3 g of dimethyloxalate in 40 ml of methanol was added dropwise to the mixture over 30 minutes and the resulting mixture heated to reflux for 7 hours. The mixture was concentrated under reduced pressure, diluted with 240 ml of water, and then cooled in an ice bath. The reaction mixture was adjusted to pH 6.5 with 10 % hydrochloric acid. The precipitated solids were collected by filtration, washed with water, and dried to give 4.5 g of the title compound as a white solid.

IR (KBr, cm$^{-1}$) : 3230; 1709; 1383.
NMR (DMSO-d$_6$) 12.1(2H,s); 8.4(1H,s); 8.2(1H,d); 7.05 (1H,d).

PREPARATION 2

Preparation of
1-methyl-2,3(4H)-dioxo-pyrazino-5,6-c]pyridine

3-Amino-4-methylaminopyridine was reacted in the manner similar to that described in Preparation 1 to give the title compound.

IR (cm$^{-1}$): 3433; 1707; 1420.
NMR (DMSO-d$_6$): 12.1(1H,s); 8 4(1H,s); 8.3(1H,d); 7.4(1H,d); 3.5(3H,s).

PREPARATION 3

Preparation of
4-methyl-2,3(1H)-dioxo-pyrazino-[5,6-c]pyridine 3-methylamino-4-aminopyridine was reacted in the manner similar to that described in Preparation 1 to give the title compound.

IR (KHr, cm$^{-1}$): 3225; 1708; 1380.
NMR (DMSO-d$_6$): 8.55(1H,s); 8.26(1H,d); 7.09(1H,d); 3.53(3H,s).

PREPARATION 4

Preparation of
1-ethyl-2.3(4H)-dioxo-pyrazino-5,6-c]pyridine

3-Amino-4-ethylaminopyridine was reacted in the manner similar to that described in Preparation 1 to give the title compound.

IR. (cm$^{-1}$): 1703; 1612; 1391.
NMR (DMSO-d$_6$): 12.1(1H,s); 8.4(1H,s); 8.3(1H,d); 7.4(1H,d); 4.0(2H,q); 1.2(3H,t)

PREPARATION 5

Preparation of
1-cyclopropyl-2,3(4H)-dioxo-pyrazino5,6-c]pyridine

3-Amino-4-cyclopropylaminopyridine was reacted in the manner similar to that described in Preparation 1 to give the title compound.

IR (cm$^{-1}$): b 1707; 1612; 1416.
NMR (DMSO-d$_6$): 12.1(1H,s); 8.4(1H,s); 8.3(1H,d); 7.4(1H,d); 3.5(1H,m); 0.5(4H,m).

PREPARATION 6

Preparation of 2(1H,3H)-oxo-imidazo[4,5-c]-pyridine

A mixture of 3 g of 3,4-diaminopyridine, 1.65 g of urea, and 30 ml of N,N-dimethylformamide was heated to reflux for 6 hours. The reaction mixture was cooled to room temperature and stirred for 12 hours. The precipitated solids were collected by filtration and dissolved in 30 ml of methanol. The resultant solution was treated with active carbon and evaporated under reduced pressure to give 3.1 g of the title compound as a white solid.

m.p 315° C. (decomp.)
IR (KBr, cm$^{-1}$) : 3125; 1717; 1630.
NMR (DMSO-d$_6$) 8.14(1H,s); 8 10(1H,d, J=5.19Hz); 6.97 (1H,d, J=5.19Hz).

PREPARATION 7

Preparation of
1-methyl-2(3H)-oxo-imidazo-[4,5-c]pyridine

3-Amino-4-methylaminopyridine was reacted in the manner similar to that described in Preparation 6 to give the title compound.

m.p. : 263°-265° C.
IR (KBr,cm$^{-1}$) : 2739; 1715; 1624.
NMR (D$_2$O) : 8.18(1H,s); 8.13(1H,d, J=5.3Hz); 7.1(1H,d, J=5.3Hz); 3.27(3H,s).

PREPARATION 8

Preparation of
1-amino-2(3H)-oxo-imidazo-[4,5-c]pyridine
Hydrochloride

3-Amino-4-hydrazinopyridine was reacted in the manner similar to that described in Preparation 6 to give the title compound.

m.p. : 309°-310° C. (decomp.)
IR (KBr, cm$^{-1}$) : 3236; 3144; 3077; 1739; 1723.
NMR (D$_2$O): 7.55-8.45(2H,2d, J=6.0 Hz); 84.9(1H,s); 9.50(NH,bs); 12.5(NH$_2$,bs).

PREPARATION 9

Preparation of
2-(1-hydroxyethyl)-2(3H)-oxo-imidazo[4,5-c]pyridine

3-Amino-4-(2-hydroxyethyl)aminopyridine was reacted in the manner similar to that described in Preparation 6 to give the title compound.

IR (KBr, cm$^{-1}$) : 3400; 3144; 1740; 1715.

NMR (D$_2$O) : 7.55-8.45(2H,2d); 8.5(1H,s); 9.5(NH,bs); 3.3-3.5(4H,dd).

PREPARATION 10

Preparation of 2(1H,3H)-oxo-imidazo[4,5-b]-pyridine 2,3-Diaminopyridine was reacted in the manner similar to that described in Preparation 6 to give the title compound.

m.p. : 270°-272° C.
IR (KBr, cm$^{-1}$) : 3462; 1692; 1434.
NMR (DMSO-d$_6$): 11.2(1H,s); 10.71(1H,s); 7.85(1H,s, J=1.6, 5.1Hz); 7.20(1H,s, J=1.6, 7.7Hz); 3.33(3H,s).

EXAMPLE 1

Synthesis of
7-β-[(Z)-2-(2-aminothiazol-4-yl)-2-methoxyiminoacetamido]-3-[2,3(1H,4H)-dioxo-pyrazino[5,6-c]-pyridiniummethyl]-3-cephem-4-carboxylate To a suspension of 500 mg of 7-β-[(Z)-2-(2-aminothiazol-4-yl)-2-methoxyiminoacetamido]-3-acetoxymethyl-3-cephem-4-carboxylic acid in 10 ml of well-dried dichloromethane was added, in one portion, 0.80 ml of N-methyl-N-(trimethylsilyl)trifluoroacetamide at room temperature. The reaction mixture was stirred for 5 minutes at 25° C. under a nitrogen atmosphere. To the stirred solution was added by pipette 0.50 ml of iodotrimethylsilane at 0° C., and the reaction mixture was then stirred at room temperature for 30 minutes. Thereafter, the solvent was evaporated off under reduced pressure to provide an oil. The oil was dissolved in a mixture of 10 ml of acetonitrile and 1.0 ml of tetrahydrofuran, and the solution was stirred for 5 minutes. The stirred solution was added, in one portion, to a solution of 180 mg of 2,3(1H,4H)-dioxo-pyrazino[5,6-c]pyridine silylated with 0.80 ml of N,O-bis(trimethylsilyl)acetamide in 10 ml of acetonitrile. The reaction mixture was stirred for 3 hours at 25° C. and then added to a mixture of 1.0 ml of methanol and 2 ml of acetonitrile at 0° C. The mixture was stirred at 0° C. for 30 minutes. The precipitated solids were collected by filtration to give a solid product. 10 ml of water was added to the solid, and the mixture was neutralized with saturated sodium bicarbonate solution and then concentrated. The residue was purified by chromatography over silica gel to give 100 mg of the title compound.

m.p. 210° C. (decomp.)
IR (KBr, cm$^{-1}$): 1771; 1685; 1618.
NMR (DMSO-d$_6$): 9.55(1H,d); 8.5(2H,m); 7.4(1H,d); 6.9(1H,s); 5.85(1H,dd, J=6Hz); 5.1(1H,d, J=6Hz); 3.8(3H,s).

EXAMPLE 2

Synthesis of
7-β-(Z)-2-(2-aminothiazol-4-yl)-2-ethoxyiminoacetamido]-3-[2,3(1H,4H)-dioxo-pyrazino[5,6-c]-pyridiniummethyl1-3-cephem-4-carboxylate 510 Mg of 7-β-[(Z)-2-(2-aminothiazol-4-yl)-2-ethoxyiminoacetamido]-3-acetoxymethyl-3-cephem-4-carboxylic acid was suspended in 10 ml of dry dichloromethane and reacted with 0.8 ml of N-methyl-N-(trimethylsilyl)trifluoroacetamide and then 0.5 ml of iodotrimethylsilane in the same manner as described in Example 1. The reaction mixture was concentrated. The concentrate was dissolved in a mixture of 10 ml of acetonitrile and 1 ml of tetrahydrofuran to give a solution. Separately, 200 mg of 2,3(1H,4H)-dioxo-pyrazino-[5,6-c]pyridine was reacted with 0.8 ml of N,O-bistrimethylsilylacetamide in 5 ml of acetonitrile to give a silylated pyridine derivative, which was then added to the solution previously obtained. The mixture was reacted at room temperature for 3 hours. Then, to the reaction mixture, 1 ml of methanol was added to effect deprotection. The precipitated solids were filtered out and purified to give 200 mg of the title compound.

m.p.: 208° C. (decomp.)
IR (cm$^{-1}$): 1773; 1687; 1620.
NMR (DMSO-d$_6$): 9.55(1H,d); 8.5(2H,m); 7.4(1H,d); 6.9(1H,s); 5.85(1H,dd, J=6Hz); 5.1(1H,d, J=6Hz); 4.4(2H,q); 1.4(3H,t).

EXAMPLE 3

Synthesis of
7-β-[(Z)-2)-aminothiazol-4-yl)-2-propynyloxyiminoacetamido]-3-[2,3(1,H,4H)-dioxo-pyrazino-[5,6c]pyridiniummethyl]-3-cephem-4-carboxylate 500 mg of 7-β-[(Z)-2-(2-aminothiazol-4-yl)-2-propynyloxyiminoacetamido]-3-acetoxymethyl-3-cephem-4-carboxylic acid was suspended in 10 ml of dry dichloromethane and reacted with 0.8 ml of N-methyl-N-(trimethylsilyl)trifluoroacetamide and then 0.5 ml of iodotrimethylsilane in the same manner as described in Example The reaction mixture was concentrated. The concentrate was dissolved in a mixture of 10 ml of acetonitrile and 1 ml tetrahydrofuran to give a solution. Separately, 200 mg of 2,3(1H,4H)-dioxo-pyrazino[5,6-c]pyridine was reacted with 0.8 ml of N,O-bistrimethylsilylacetamide in 5 ml of acetonitrile to give a silylated pyridine derivative, which was then added to the solution previously obtained. The mixture was reacted at room temperature for 3 hours. Then, to the reaction mixture, 1 ml of methanol was added to effect deprotection. The precipitated solids were filtered out and purified to give 210 mg of the desired compound.

m.p. 220° C. (decomp.)

IR (cm$^{-1}$): 1773; 1690; 1620.

NMR (DMSO-d$_6$): 9.6(1H,d); 8.55(2H,m); 7.4(1H,d); 6.9(1H,s); 5.8(1H,dd, J=6Hz); 5.1(1H,d, J=6Hz); 4.7(2H,m)

EXAMPLE 4

Synthesis of 7-β-[(Z)-2-(2-aminothiazol-4-yl)-2-cyclopropylmethoxyiminoacetamido]-3-[2,3(1H,4H)-dioxopyrazino[5,6-c]pyridiniummethyl]-3–cephem-4–carboxylate 540 Mg of 7-β-[(Z)-2-(2-aminothiazol-4-yl)-2-cyclopropylmethoxyiminoacetamido]-3-acetoxymethyl-3-cephem-4-carboxylic acid was suspended in 10 ml of dry dichloromethane and reacted with 0.8 ml of N-methyl-N-(trimethylsilyl)-trifluoroacetamide and then 0.5 ml of iodotrimethylsilane in the same manner as described in Example 1. The reaction mixture was concentrated. The concentrate was dissolved in a mixture of 10 ml of acetonitrile and 1 ml tetrahydrofuran to give a solution. Separately, 200 mg of 2,3(1H,4H)-dioxo-pyrazino[5,6-c]pyridine was reacted with 0.8 ml of N,O-bistrimethylsilylacetamide in 5 ml of acetonitrile to give a silylated pyridine derivative, which was then added to the solution previously obtained. The mixture was reacted at room temperature for 3 hours. Then, to the reaction mixture, 1 ml of methanol was added to effect deprotection. The precipitated solids were filtered out and purified to give 230 mg of the title compound.

m.p.: 215° C. (decomp.)

IR (cm$^{-1}$): 1774; 1690.

NMR (DMSO-d$_6$): 9.6(1H,d); 8.55(2H,m); 7.4(1H,d); 6.9(1H,s); 5.8(1H,dd, J=6Hz); 5.1(1H,d, J=6Hz); 4.3(2H,d); 0.5–1.0(4H,m).

EXAMPLE 5

Synthesis of 7-β-[(Z)-2-(2-aminothiazol-4-yl)-2-carboxymethoxyiminoacetamido-3-[2,3(1H,4H)-dioxo-pyrazino-[5,6-c]pyridiniummethyl)-3–cephem-4–carboxylate 530 Mg of 7-β-[(Z)-2-(2-aminothiazol-4-yl)-2-carboxymethoxyiminoacetamido]-3-acetoxymethyl-3-cephem-4-carboxylic acid was suspended in 15 ml of dry dichloromethane and reacted with 1 ml of N-methyl-N-(trimethylsilyl)trifluoroacetamide and then 0.5 ml of iodotrimethylsilane in the same manner as described in Example 1. The reaction mixture was concentrated. The concentrate was dissolved in a mixture of 15 ml of acetonitrile and 1 ml of tetrahydrofuran to give a solution. Separately, 200 mg of 2,3(1H,4H)-dioxo-pyrazino-[5,6-c]pyridine was reacted with 0.8 ml of N,O-bistrimethylsilylacetamide in 5 ml of acetonitrile to give a silylated pyridine derivative, which was then added to the solution previously obtained. The mixture was reacted at room temperature for 3 hours. Then, to the reaction mixture, 1 ml of methanol was added to effect deprotection. The precipitated solids were filtered out and purified to give 250 mg of the title compound.

m.p.: 218° C. (decomp.)

IR (cm$^{-1}$): 1772; 1687.

NMR (DMSO-d$_6$) 9.6(1H,d); 8.5(2H,m); 7.4(1H,d); 6.9(1H,s); 5.8(1H,dd, J=6Hz); 5.1(1H,d, J=6Hz); 4.6(2H,s).

EXAMPLE 6

Synthesis of 7-β-[(Z)-2-(2-aminothiazol-4-yl)-2-(2-carboxyprop-2-yl)oxyiminoacetamido1-3-[2,3(1H,4H)-dioxopyrazino[5,6-c]pyridiniummethyl1-3–cephem-4–carboxylate 560 Mg of 7-β-[(Z)-2-(2-aminothiazol-4-yl)-2-(2-carboxyprop-2-yl)oxyiminoacetamido]-3-acetoxymethyl-3-cephem-4-carboxylic acid was suspended in 15 ml of dry dichloromethane and reacted with 1 ml of N-methyl-N-(trimethylsilyl)trifluoroacetamide and then 0.5 ml of iodotrimethylsilane in the same manner as described in Example 1. The reaction mixture was concentrated. The concentrate was dissolved in a mixture of 15 ml of acetonitrile and I ml of tetrahydrofuran to give a solution. Separately, 200 mg of 2,3(1H,4H)-dioxo-pyrazino-[5,6-c]pyridine was reacted with 0.8 ml of N,O-bistrimethylsilylacetamide in 5 ml of acetonitrile to give a silylated pyridine derivative, which was then added to the solution previously obtained. The mixture was reacted at room temperature for 3 hours. Then, to the reaction mixture, ml of methanol was added to effect deprotection. The precipitated solids were filtered out and purified to give 250 mg of the title compound.

m.p.: 220° C. (decomp.)

IR (cm$^{-1}$): 1773; 1692.

NMR (DMSO-d$_6$) 9.55(1H,d); 8.55(2H,m); 7.4(1H,d); 6.9 (1H,s); 5.8(1H,dd, J=6Hz); 5.1(1H,d, J=6Hz); 1.5(6H,s).

EXAMPLE 7

Synthesis of 7-β-[(Z)-2-(2-aminothiazol-4-yl)-2-methoxyiminoacetamidol-3-[1-methyl-2,3(4H)-dioxo-pyrazino-5,6-c]pyridiniummethyl1-3–cephem-4–carboxylate 500 Mg of 7-β-[(Z)-2-(2-aminothiazol-4-yl)-2-methoxyiminoacetamido]-3-acetoxymethyl-3-cephem-4-carboxylic acid was suspended in 10 ml of dry dichloromethane was reacted with 0.8 ml of N-methyl-N-(trimethylsilyl)trifluoroacetamide and then 0.5 ml of iodotrimethylsilane in the same manner as described in Example The reaction mixture was concentrated. The concentrate was dissolved in a mixture of 10 ml of acetonitrile and 1 ml of tetrahydrofuran to give a solution. Separately, 240 mg of 1-methyl-2,3(4H)-dioxopyrazino[5,6-c]pyridine was reacted with 0.8 ml of N,O-bistrimethylsilylacetamide in 5 ml of acetonitrile to give a silylated pyridine derivative, which was then added to the solution previously obtained. The mixture was reacted at room temperature for 3 hours. Then, to the reaction mixture, 1 ml of methanol was added to effect deprotection. The precipitated solids were filtered out and purified to give 250 mg of the title compound.

m.p.: 205° C. (decomp.)

IR (cm$^{-1}$): 1775; 1714.

NMR (DMSO-d$_6$): 9.6(1H,d); 8.5(2H,m); 7.4(1H,d); 6.9(1H,s); 5.8(1H,dd, J=6Hz); 5.15(1H,d, J=6Hz); 3.8 (3H,s); 3.5(3H,s).

EXAMPLE 8

Synthesis of
7-β-(Z)-2-(2-aminothiazol-4-yl)-2-methoxyiminoacetamido1-3-[1-ethyl-2,3(4H)-dioxo-pyrazino-5,6-c]pyridiniummethyl1-3-cephem-4-carboxylate 500 Mg of 7-β-[(Z)-2-(2-aminothiazol-4-yl)-2-methoxyiminoacetamido]-3-acetoxymethyl-3-cephem-4-carboxylic acid was suspended in 10 ml of dry dichloromethane and reacted with 0.8 ml of N-methyl-N-(trimethylsilyl)trifluoroacetamide and then 0.5 ml of iodotrimethylsilane in the same manner as described in Example 1 The reaction mixture was concentrated. The concentrate was dissolved in a mixture of 10 ml of acetonitrile and 1 ml of tetrahydrofuran to give a solution. Separately, 250 mg of 1-ethyl-2,3(4H)-dioxopyrazino[5,6-c]-pyridine was reacted with 0.8 ml of N,O-bistrimethylsilylacetamide in 5 ml of acetonitrile to give a silylated pyridine derivative, which was then added to the solution previously obtained. The mixture was reacted at room temperature for 3 hours. Then, to the reaction mixture, 1 ml of methanol was added to effect deprotection. The precipitated solids were filtered out and purified to give 250 mg of the title compound.

m.p.: 210° C. (decomp )
IR (cm$^{-1}$): 1775; 1716.
NMR (DMSO-d$_6$): 9.6(1H,d); 8.5(2H,m); 7.4(1H,d); 6.9(1H,s); 5.8(1H,dd, J=6Hz); 5.2(1H,d, J=6Hz); 3.8 (3H,s); 4.0(2H,q); 1.2(3H,t).

EXAMPLE 9

Synthesis of
7-β-[(Z)-2-(2-aminothiazol-4-yl)-2-methoxyiminoacetamido]-3-[1-cyclopropyl-2,3(4H)-dioxopyrazino-[5,6-c]pyridiniummethyl]-3-cephem-4-carboxylate 500 Mg of 7-β-[(Z)-2-(2-aminothiazol-4-yl)-2-methoxyiminoacetamido]-3-acetoxymethyl-3-cephem-4-carboxylic acid was suspended in 10 ml of dry dichloromethane was reacted with 0.8 ml of N-methyl-N-(trimethylsilyl)trifluoroacetamide and then 0.5 ml of iodotrimethylsilane in the same manner as described in Example 1. The reaction mixture was concentrated. The concentrate was dissolved in a mixture of 10 ml of acetonitrile and 1 ml of tetrahydrofuran to give a solution. Separately, 270 mg of 1-cyclopropyl-2,3(4H)-dioxopyrazino[5,6-c]pyridine was reacted with 0.8 ml of N,O-bistrimethylsilylacetamide in 5 ml of acetonitrile to give a silylated pyridine derivative, which was then added to the solution previously obtained. The mixture was reacted at room temperature for 3 hours. Then, to the reaction mixture, 1 ml of methanol was added to effect deprotection. The precipitated solids were filtered out and purified to give 230 mg of the title compound.

m.p.: 208° C. (decomp.)
IR (cm$^{-1}$): 1774; 1716
NMR (DMSO-d$_6$): 9.6(1H,d); 8.5(2H,m); 7.4(1H,d); 6.9(1H,s); 5.8(1H,dd, J=6Hz); 5.2(1H,d, J=6Hz); 3.8 (3H,s); 3.5(1H,m), 0.6(4H,m).

EXAMPLE 10

Synthesis of
7-β-1(Z)-2-(2-aminothiazol-4-yl)-2-(2-carboxyprop-2-yl)oxyiminoacetamido[-3-[1-methyl-2,3(4H)-dioxopyrazino[5,6-c]pyridiniummethyl)-3-cephem-4-carboxylate 560 Mg of 7-β-[(Z)-2-(2-aminothiazol-4-yl)-2-(2-carboxy-prop-2-yl)oxyiminoacetamido]-3-acetoxymethyl-3-cephem-4-carboxylic acid was suspended in 15 ml of dry dichloromethane and reacted with 1 ml of N-methyl-N-(trimethylsilyl)trifluoroacetamide and then 0.5 ml of iodotrimethylsilane in the same manner as described in Example 1. The reaction mixture was concentrated. The concentrate was dissolved in a mixture of 15 ml of acetonitrile and 1 ml of tetrahydrofuran to give a solution. Separately, 240 mg of 1-methyl-2,3(4H)-dioxopyrazino[5,6-c]pyridine was reacted with 0.8 ml of N,O-bistrimethylsilylacetamide in 5 ml of acetonitrile to give a silylated pyridine derivative, which was then added to the solution previously obtained. The mixture was reacted at room temperature for 3 hours. Then, to the reaction mixture, 2 ml of methanol was added to effect deprotection. The precipitated solids were filtered out and purified to give 200 mg of the title compound.

m.p.: 215° C. (decomp.)
IR (cm$^{-1}$): 1773; 1715.
NMR (DMSO-d$_6$): 9.6(1H,d); 8.55(2H,m); 7.4(1H,d); 6.9(1H,s); 5.8(1H,dd, J=6Hz); 5.2(1H,d, J=6Hz); 3.5 (3H,s); 1.5(6H,s).

EXAMPLE 11

Synthesis of
7-β-[(Z)-2-(2-aminothiazol-4-yl)-2-2-carboxyprop-2-yl)oxyiminoacetamido]-3-[1-ethyl-2,3(4H)-dioxopyrazino[5,6-c]pyridiniummethyl1-3-cephem-4-carboxylate 560 Mg of 7-β-[(Z)-2-(2-aminothiazol-4-yl)-2-(2-carboxyprop-2-yl)oxyiminoacetamido]-3-acetoxymethyl-3-cephem-4-carboxylic acid was suspended in 15 ml of dry dichloromethane and reacted with 1 ml of N-methyl-N-(trimethylsilyl)trifluoroacetamide and then 0.5 ml of iodotrimethylsilane in the same manner as described in Example 1. The reaction mixture was concentrated. The concentrate was dissolved in a mixture of 15 ml of acetonitrile and 1 ml of tetrahydrofuran to give a solution. Separately, 250 mg of 1-ethyl-2,3(4H)-dioxopyrazino[5,6-c]pyridine was reacted with 0.8 ml of N,O-bistrimethylsilylacetamide in 5 ml of acetonitrile to give a silylated pyridine derivative, which was then added to the solution previously obtained. The mixture was reacted at room temperature for 3 hours. Then, to the reaction mixture, 2 ml of methanol was added to effect deprotection. The precipitated solids were filtered out and purified to give 230 mg of the title compound.

m.p.: 217° C. (decomp.)
IR (cm$^{-1}$): 1774; 1717.
NMR (DMSO—d$_6$): 9.6(1H,d); 8.5(2H,m); 7.4(1H,d); 6.9(1H,s); 5.8(1H,dd, J=6Hz); 5.2(1H,d, J=6Hz); 4.0 (2H,q); 1.5(6H,s); 1.2(3H,t).

EXAMPLE 12

Synthesis of
7-β-[(Z)-2-(2-aminothiazol-4-yl)-2-(2-carboxyprop-2-yl)oxyiminoacetamido]-3-[1-cyclopropyl-2,3(4H)-dioxo-pyrazino[5,6-c]pyridiniummethyl1-3-cephem-4-carboxylate 560 Mg of 7-B-[(Z)-2-(2-aminothiazol-4-yl)-2-(2-carboxyprop-2-yl)oxyiminoacetamido]-3-acetoxymethyl-3-cephem-4-carboxylic acid was suspended in 15 ml of dry dichloromethane and reacted with 1 ml of N-methyl-N-(trimethylsilyl)trifluoroacetamide and then 0.5 ml of iodotrimethylsilane in the same manner as described in Example 1. The reaction mixture was concentrated. The concentrate was dissolved in a mixture of 15 ml of acetonitrile and 1 ml of tetrahydrofuran to give a solution. Separately, 270 mg of 1-cyclopropyl-2,3(4H)-dioxopyrazino[5,6-c]pyridine was reacted with 0.8 ml of N,O-bistrimethylsilylacetamide in 5 ml of acetonitrile to give a silylated pyridine derivative, which was then added to the solution previously obtained. The mixture was reacted at room temperature for 3 hours. Then, to the reaction mixture, 2 ml of methanol was added to effect deprotection. The precipitated solids were filtered out and purified to give 250 mg of the title compound.

m.p. 215° C. (decomp.)

IR (cm$^{-1}$): 1775; 1716.

NMR (DMSO—d$_6$): 9.6(1H,d); 8.5(2H,m); 7.4(1H,d); 6.9(1H,s); 5.8(1H,dd, J=6Hz); 5.2(1H,d, J=6Hz); 3.5(1H,m); 1.5(6H,s); 0.6(4H,m).

EXAMPLE 13

Synthesis of
7-β-[(Z)-2-(2-aminothiazol-4-yl)-2-methoxyiminoacetamido]-3-[4-methyl-2,3(1H)-dioxo-pyrazino-[5,6-c]pyridiniummethyl-3-cephem-4-carboxylate To a suspension of 340 mg of 7-β-[(z)-2-(2-aminothiazol-4-yl)-2-methoxyiminoacetamido]-3-acetoxymethyl-3-cephem-4-carboxylic acid in 10 ml of dry dichloromethane was added, in one portion, 0.5 ml of N-methyl-N-(trimethylsilyl)trifluoroacetamide at room temperature. The reaction mixture was stirred for 5 minutes at 25° C. under a nitrogen atmosphere. To the stirred solution was added 0.24 ml of iodotrimethylsilane at 0° C. and the reaction mixture was then stirred at room temperature for 30 minutes. The solvent was removed by evaporation under reduced pressure to give an oil. The oil was dissolved in a mixture of 10 ml of acetonitrile and 1 ml of tetrahydrofuran. The resultant solution was stirred for 5 minutes. The stirred solution was added, in one portion, to a solution of 4-methyl-2,3(1H)-dioxo-pyrazino[5,6-c]pyridine silylated with 0.8 ml of N,O-bis(trimethylsilyl)acetamide in 10 ml of acetonitrile. The reaction mixture was stirred for 3 hours at 25° C. and then added to a mixture of 1.0 ml of methanol and 2 ml of acetonitrile at 0° C. The precipitated solids were collected by filtration to give a solid product. 10 Ml of water was added to the solid, and the mixture was neutralized with a saturated NaHCO$_3$ solution and then concentrated. The resultant residue was purified by chromatography over silica gel eluting with acetonitrile:H$_2$O (4:1) and concentrated to give 40 mg of the title compound.

m.p. 220° C. (decomp.)

IR (KBr, cm$^{-1}$): 1760; 1620.

NMR (DMSO—d$_6$) 9.7(1H,d, J=7.8Hz); 8.5(1H,s); 8.3(1H,d); 7.10(1H,d); 6.8(1H,s); 5.6(1H,dd, J=7.8, 4.5Hz); 5.1(1H,d, J=4.86Hz); 4.9(2H,bs); 3.75(3H,s); 3.5(3H,s): 3.4(2H,m).

EXAMPLE 14

Synthesis of
7-β-[(Z)-2-(aminothiazol-4-yl)-2-fluoromethoxyiminoacetamido]-3-[2,3(1H,4H)-dioxo-pyrazino-5,6-c]pyridiniummethyl]-3-cephem-4-carboxylate To a suspension of 700 mg of 7-β-[(z)-2-(2-aminothiazol-4-yl)-2-fluoromethoxyiminoacetamido]-3-acetoxymethyl-3-cephem-4-carboxylic acid in 15 ml of dry dichloromethane was added, in one portion, 1.0 ml of N-methyl-N-(trimethylsilyl)trifluoroacetamide at room temperature. The reaction mixture was stirred for 5 minutes at 25° C. under a nitrogen atmosphere. To the stirred solution was added by pipette 0.44 ml of iodotrimethylsilane at 0° C., and the reaction mixture was then stirred at room temperature for 30 minutes. Thereafter, the mixture was evaporated under reduced pressure to remove the solvent and then provide an oil. The oil was dissolved in a mixture of 10 ml of acetonitrile and 1.0 ml of tetrahydrofuran, and the solution was stirred for 5 minutes. The stirred solution was added in one portion to a solution of 400 mg of 2,3(1H,4H)-dioxo-pyrazino[5,6-c]pyridine silylated with 0.88 ml of N,O-bis(trimethylsilyl)acetamide in 10 ml of acetonitrile. The reaction mixture was stirred for 3 hours at 25° C. and then added to a mixture of 1.0 ml of methanol and 2 ml of acetonitrile at 0° C. The mixture was stirred at 0° C. for 30 minutes. The precipitated solids were collected by filtration to give a solid product. 10 Ml of water was added to the solid, and the mixture was neutralized with a saturated sodium bicarbonate solution and then concentrated. The residue was purified by chromatography over silica gel to give 250 mg of the title compound.

m.p.: 220° C. (decomp.)

IR (KBr, cm$^{-1}$) 1770; 1688; 1619.

NMR (DMSO—d$_6$): 9.72(1H,bd, J=7.84Hz); 8.51(1H,s); 8.35 (1H,bs); 7.10(1H,d, J=5.7Hz); 6.88(1H,s); 6.32(2H,d, J=55.18Hz); 5.65(1H,dd, J=7.84, 4.87Hz); 5.05(1H,d, J=4.87Hz); 4.95 (2H,bs); 3.44(2H,m).

EXAMPLE 15

Synthesis of
7-β-[(Z)-2-(2-aminothiazol-4-yl)-2-methoxyiminoacetamido-3-2(1H,3H)-oxo-imidazo[4,5-c]-pyridiniummethyl]-3-cephem-4-carboxylate To a suspension of 500 mg of 7-β-[(Z)-2-(2-aminothiazol-4-yl)-2-methoxyiminoacetamido]-3-acetoxymethyl-3-cephem-4-carboxylic acid in 10 ml of dry dichloromethane was added, in one portion, 0.7 ml of N-methyl-N-(trimethylsily)trifluoroacetamide at room temperature. The reaction mixture was stirred for 5 minutes at 25° C. under a nitrogen atmosphere. To the stirred solution was added by pipette 0.38 ml of iodotrimethylsilane at 0° C., and the reaction mixture was then stirred at room temperature for 30 minutes. Thereafter, the reaction mixture was evaporated under reduced pressure to remove the solvent and then give an oil. The oil was dissolved in a mixture of 10 ml of acetonitrile and 1 ml of tetrahydrofuran. The resultant solution was stirred for 5 minutes. The stirred solution was added, in one portion, to a solution of 100 mg of 2(1H,3H)-oxo-imidazo[4,5-c]pyridine silylated with 0.62 ml of N,O-bis(trimethylsilyl)acetamide in 10 ml of acetonitrile. The reaction mixture was stirred for 3 hours at 25° C. and then added to a mixture of 0.5 ml of methanol and 5 ml of acetonitrile at 0° C. The precipitated solids were collected by filtration to provide a solid product. 10 Ml of water was added to the solid, and the mixture was neutralized with a saturated NaHCO$_3$ solution and then concentrated. The resultant residue was purified by chromatography over silica gel eluting with acetonitrile:H$_2$O (4:1) and concentrated to give 170 mg of the title compound.

m.p. : 219° C. (decomp.)

IR (KBr, cm$^{-1}$) : 1772; 1653; 1636.

NMR (DMSO—d$_6$) : 3.18(1H,d, J = 17 1Hz); 3.53(1H, m); 3.58 (1H,d, J = 17.1Hz); 3.78(3H,s); 4.77(1H,m); 5.06(1H,d); 5.61(1H,dd); 6.70(1H,s); 7.18(1H,bd, J = 6.85Hz); 8.48(1H,bd, J = 6.85Hz); 8.85(1H,s); 9.48(1H,dd).

EXAMPLE 16

Synthesis of 7-β-[(Z)-2-(2-aminothiazol-4-yl)-2-methoxyiminoacetamido]-3-[1-methyl-2(3H)-oxo-imidazo4,5-c]-pyridiniummethyl]-3-cephem-4-carboxylate To a suspension of 450 mg of 7-β-[(Z)-2-(2-aminothiazol-4-yl)-2-methoxyiminoacetamido]-3-acetoxymethyl-3-cephem-4-carboxylic acid in 10 ml of dry dichloromethane was added, in one portion, 0.5 ml of N-methyl-N-(trimethylsilyl)trifluoroacetamide at room temperature. The reaction mixture was stirred for 5 minutes at 25° C. under a nitrogen atmosphere. To the stirred solution was added by pipette 0.24 ml of iodotrimethylsilane at 0° C., and the reaction mixture was then stirred at room temperature for 30 minutes. Thereafter, the mixture was evaporated under reduced pressure to remove the solvent and then give an oil. The oil was dissolved in a mixture of 10 ml of acetonitrile and 1 ml of tetrahydrofuran. The resultant solution was stirred for 5 minutes. The stirred solution was added, in one portion, to a solution of 90 mg of 1-methyl-2(3H)-oxo-imidazo[4,5-c]pyridine silylated with 0.5 ml of N,O-bis(trimethylsily)acetamide in 10 ml of acetonitrile. The reaction mixture was stirred for 3 hours at 25° C. and then added to a mixture of 0.5 ml of methanol and 5 ml of acetonitrile at 0° C. The mixture was stirred at 0° C. for 30 minutes. The precipitated solids were collected by filtration to give a solid product. 10 Ml of water was added to the solid, and the mixture was neutralized with a saturated sodium bicarbonate solution and then concentrated. The residue was purified by chromatography over silica gel to give 50 mg of the title compound.

m.p.: 250° C. (decomp.)

cm$^{-1}$) 1760; 1616; 1590.

NMR (D$_2$O): 8.34(1H,s); 8.1(1H,s); 7.35(1H,d); 7.00 (1H,s); 5.9(1H,d); 5.15(1H,d); 4.60(2H,q); 3.80(2H,q); 3.35(2H,q); 3.15(3H,s).

EXAMPLE 17

Synthesis of 7-β-[(Z)-2-(2-aminothiazol-4-yl)-2-methoxyiminoacetamido]-3-[1-amino-2(3H)-oxo-imidazo[4,5-c]-pyridiniummethyl]-3-cephem-4-carboxylate To a suspension of 650 mg of 7-β-[(z)-2-(aminothiazol-4-ly)-2-methoxyiminoacetamido]-3-acetoxymethyl-3-cephem-4-carboxylic acid in 15 ml of dry dichloromethane was added, in one portion, 7.8 ml of N-methyl-N-(trimethylsily)trifluoroacetamide at room temperature. The reaction mixture was stirred for 5 minutes at 25° C. under a nitrogen atmosphere. To the stirred solution were added by pipette 0.49 ml of iodotrimethylsilane at 0° C., and the reaction mixture was then stirred at room temperature for 30 minutes. Thereafter, the mixture was evaporated under reduced pressure to remove the solvent and then give an oil. The oil was dissolved in a mixture of 10 ml of acetonitrile and 1 ml of tetrahydrofuran, and the resulting solution was stirred for 5 minutes. The stirred solution was added, in one portion, to a solution of 165 mg of 1-amino-2(3H)-oxo-imidazo[4,5-c]pyridine silylated with 8.2 ml of N,O-bis(trimethylsilyl)acetamide in 10 ml of acetonitrile. The reaction mixture was stirred for 3 hours at 25° C. and then added to a mixture of 0.5 ml of methanol and 5 ml of acetonitrile at 0° C. The mixture was stirred at 0° C. for 30 minutes. The precipitated solids were collected by filtration to give a solid product. 10 Ml of water was added to the solid and the mixture was neutralized with a saturated sodium bicarbonate solution and then concentrated. The residue was purified by chromatography over silica gel to give 120 mg of the title compound.

m.p.: 224° C. (decomp.)

IR (KBr, cm$^{-1}$): 1785; 1653.

NMR (DMSO—d$_6$): 9.6(1H,d, J = 7.6Hz); 8.9(1H,s); 8.6(1H,d, J = 6.6Hz); 7.5(1H,d, J = 6.6Hz); 7.2(2H,b); 6.7(1H,m); 6.6(2H,bd); 5.8(1H,dd, J = 7.8, 5.0Hz); 5.1(1H,d, J = 5.0Hz); 5.4(2H,bd); 6.6(2H,bd); 3.8(3H,s); 3.4(2H,m).

EXAMPLE 18

Synthesis of 7-β-[(Z)-2-(2-aminothiazole-4-yl)-2-methoxyiminoacetamido]-3-[1-(2-hydroxyethyl)-2(3H)-oxo-imidazo-[4,5-c]pyridiniummethyl]-3-cephem-4-carboxylate To a suspension of 700 mg of 7-β-[(Z)-2-(2-aminothiazol-4-yl)-2-methoxyiminoacetamido]-3-acetoxymethyl-3-cephem-4-carboxylic acid in 70 ml of dry dichloromethane was added, in one portion, 16 ml of N-methyl-N-(trimethylsilyl)trifluoroacetamide at room temperature. The reaction mixture was stirred for 5 minutes at 25° C. under a nitrogen atmosphere. To the stirred solution was added by pipette 0.5 ml of iodotrimethylsilane at 0° C., and the reaction mixture was then stirred at room temperature for 30 minutes. Thereafter, the mixture was evaporated under reduced pressure to remove the solvent and then give an oil. The oil was dissolved in a mixture of 10 ml of acetonitrile and 1 ml of tetrahydrofuran, and the solution was stirred for 5 minutes. The stirred solution was added, in one portion, to a solution of 160 mg of 1-(2-hydroxyethyl)-2(3H)-oxo-imidazo[4,5-c]pyridine silylated with 8.3 ml of N,O-bis(trimethylsilyl)acetamide in 10 ml of acetonitrile. The reaction mixture was stirred for 3 hours at 25° C. and then added to a mixture of 0.6 ml of methanol and 6 ml of acetonitrile at 0° C. The mixture was stirred at 0° C. for 30 minutes. The precipitated solids were collected by filtration to give a solid product. 70 Ml of water was added to the solid, and the mixture was neutralized with a saturated sodium bicarbonate solution and then concentrated. The residue was purified by chromatography over silica gel to give 115 mg of the title compound.

m.p. 250° C.

NMR: 9.5(1H,d); 8.7(1H,s); 8.5(1H,d); 7.4(1H,d); 7.1(1H,s); 6.7(1H,s); 5.6(1H,dd); 5 1(1H,d); 3.75(3H,s); 3.0–3.6(4H,m)

EXAMPLE 19

Synthesis of
7-β-[(Z)-2-(2-aminothiazol-4-yl)-2-methoxyiminoacetamido]-3-[2(1H,3H)-oxo-imidazo[4,5-b]-pyridiniummethyl]-3-cephem-4-carboxylate To a suspension of 500 mg of 7-β-[(Z)-2-(2-aminothiazol-4-yl)-2-methoxyiminoacetamido]-3-acetoxymethyl-3-cephem-4-carboxylic acid in 10 ml of dry dichloromethane was added, in one portion, 0.74 ml of N-methyl-N-(trimethylsilyl)trifluoroacetamide at room temperature. The reaction mixture was stirred for 5 minutes at 25° C. under a nitrogen atmosphere. To the stirred solution was added by pipette 0.39 ml of iodotrimethylsilane at 0° C., and the reaction mixture was then stirred at room temperature for 30 minutes. Thereafter, the solvent was evaporated off under reduced pressure to give an oil. The oil was dissolved in a mixture of 15 ml of acetonitrile and 0.5 ml of tetrahydrofuran, and the solution was stirred for 5 minutes. The stirred solution was added, in one portion, to a solution of 150 mg of 2(1H,3H)-oxo-imidazo[4.5-b]-pyridine silylated with 1.1 ml of N,O-bis(trimethylsily)acetamide in 3 ml of acetonitrile. The reaction mixture was stirred for 3 hours at 25° C. and then added to a mixture of 0.5 ml of methanol and 5 ml of acetonitrile at 0° C. The mixture was stirred at 0° C. for 30 minutes. The precipitated solids were collected by filtration to give a solid product. 10 Ml of water was added to the solid, and the mixture was neutralized with a saturated sodium bicarbonate solution and then concentrated. The residue was purified by chromatography over silica gel to give 110 mg of the title compound.
m.p.: 256° C. (decomp.)
IR (KBr, cm$^{-1}$): 1668; 1769.
NMR (D$_2$O): 3.3(2H,q); 3.95(3H,s); 4.66(2H,q); 5.2(1H,d, J=4.9Hz); 6.96(1H,m); 6.9(1H,s); 7.4(1H,d, J=7.4Hz); 7.75(1H,d, J=5.4Hz).

EXAMPLE 20

Synthesis of
7-β-[(Z)-2-(2-aminothiazol-4-yl)-2-fluoromethoxyiminoacetamido]-3-[2(1H.3H)-oxo-imidazo[4,5-c]-pyridiniummethyl]-3-cephem-4-carboxylate To a suspension of 700 mg of 7-β-[(Z)-2-(2-aminothiazol-4-yl)-2-fluoromethoxyiminoacetamido]-3-acetoxymethyl-3-cephem-4-carboxylic acid in 15 ml of dry dichloromethane was added, in one portion, 1.0 ml of N-methyl-N-(trimethylsilyl)trifluoroacetamide at room temperature. The reaction mixture was stirred for 5 minutes at 25° C. under a nitrogen atmosphere. To the stirred solution was added by pipette 0.44 ml of iodotrimethylsilane at 0° C., and the reaction mixture was then stirred at room temperature for 30 minutes. Thereafter, the mixture was evaporated under reduced pressure to remove the solvent and then give an oil. The oil was dissolved in a mixture of 10 ml of acetonitrile and 1.0 ml of tetrahydrofuran, and the solution was stirred for 5 minutes. The stirred solution was added in one portion to a solution of 178 mg of 2(1H,3H)-oxo-imidazo[4,5-c]pyridine silylated with 0.88 ml of N,O-bis(trimethylsily)acetamide in 10 ml of acetonitrile. The reaction mixture was stirred for 3 hours at 25° C. and then added to a mixture of 1.0 ml of methanol and 2 ml of acetonitrile at 0° C. The mixture was stirred at 0° C. for 30 minutes. The precipitated solids were collected by filtration to give a solid product. 10 Ml of water was added to the solid, and the mixture was neutralized with a saturated sodium bicarbonate solution and then concentrated. The residue was purified by chromatography over silica gel to give 110 mg of the title compound.
m.p.: 210° C. (decomp.)
IR (KBr, cm$^{-1}$): 1763; 1653; 1616.
NMR (D$_2$O): 3.18(1H,d); 3.58(1H,d); 4.41(1H,s); 4.99 (1H,s); 5.30(1H,d, J=4.80Hz); 5.81(2H,d, J=55.07Hz); 5.88(1H,d, J=4.80Hz); 7.15(1H,s); 7.46(1H,d, J=6.9Hz); 8.35(1H,d, J=6.9Hz); 8.46(1H,s).

EXAMPLE 21

Synthesis of
7-β-(Z)-2-(2-aminothiazol-4-yl)-2-fluoromethoxyiminoacetamido]-3-[1-methyl-2(3H)-oxo-imidazo-[4,5-c]pyridiniummethyl]-3-cephem-4-carboxylate To a suspension of 300 mg of 7-β-[(Z)-2-(2-aminothiazol-4-yl)-2-fluoroemthoxyiminoacetamido]-3-acetoxymethyl-3-cephem-4-carboxylic acid in 5 ml of dry dichloromethane was added, in one portion, 0.5 ml of N-methyl-N-(trimethylsilyl)trifluoroacetamide at room temperature. The reaction mixture was stirred for 5 minutes at 25° C. under a nitrogen atmosphere. To the stirred solution was added by pipette 0.3 ml of iodotrimethylsilane at 0° C., and the reaction mixture was then stirred at room temperature for 30 minutes. Thereafter, the solvent was evaporated off under reduced pressure to give an oil. The oil was dissolved in a mixture of 10 ml of acetonitrile and 0.5 ml of tetrahydrofuran, and the resultant solution was stirred for 5 minutes. The stirred solution was then added, in one portion, to a solution of 85 mg of methyl-2(3H)-oxo-imidazo[4,5-c]pyridine silylated with 0.71 ml of N,O-bis(trimethylsilyl)acetamide in 3 ml of acetonitrile. The reaction mixture was stirred for 3 hours at 25° C. and then added to a mixture of 0.3 ml of methanol and 2 ml of acetonitrile at 0° C. The mixture was stirred at 0° C. for 30 minutes. The precipitated solids were collected by filtration to give a solid product. 10 Ml of water was added to the solid, and the mixture was neutralized with a saturated sodium bicarbonate solution and then concentrated. The residue was purified by chromatography over silica gel to give 60 mg of the title compound.
m.p.: 242° C. (decomp.)
IR (KBr, cm$^{-1}$): 1533; 1616; 1751.
NMR (D$_2$O): 8.35(1H,s); 8.2(1H,s); 7.35(1H,d); 7.06 (1H,s); 5.78(2H,d, J=55.4Hz); 5.85(1H,d); 5.3(1H,d); 4.55 (2H,q); 3.35(2H,q).

EXAMPLE 22

Synthesis of
7-β-[(Z)-2-(2-aminothiazol-4-yl)-2-fluoromethoxyiminoacetamido]-3-[1-amino-2(3H)-oxo-imidazo-[4,5-c]pyridiniummethyl]-3-cephem-4-carboxylate To a suspension of 500 mg of 7-β-[(Z)-2-(2-aminothiazol-4-yl)-2-fluoromethoxyiminoacetamido]-3-acetoxymethyl-3-cephem-4-carboxylic acid in 10 ml of dry dichloromethane was added, in one portion, 0.65 ml of N-methyl-N-(trimethylsilyl)trifluoroacetamide at room temperature. The reaction mixture was stirred for 5 minutes at 25° C. under a nitrogen atmosphere. To the stirred solution was added by pipette 0.45 ml of iodotrimethylsilane at 0° C., and the reaction mixture was then stirred at room temperature for 30 minutes. Thereafter, the solvent was evaporated off under reduced pressure to give an oil. The oil was dissolved in a mixture of 10 ml of acetonitrile and 1 0 ml of tetrahydrofuran, and the solution was stirred for 5 minutes. The stirred solution was added, in one portion, to a solution of 160 mg of 1-amino- 2(3H)-oxo-imidazo[4,5-c]pyridine silylated with 0.71 ml of N,O-bis(trimethylsilyl)acetamide in 10 ml of acetonitrile. The reaction mixture was stirred for 3 hours at 25° C. and then added to a mixture of 1.0 ml of methanol and 2 ml of acetonitrile at 0° C. The mixture was stirred at 0° C. for 30 minutes. The precipitated solids were collected by filtration to give a solid product. 10 Ml of water was added to the solid and the mixture was neutralized with a saturated sodium bicarbonate solution and then concentrated. The residue was purified by chromatography over silica gel to give 105 mg of the title compound.

m.p.: 215° C. (decomp.)

IR (KBr, cm$^{-1}$): 1773; 1654.

NMR (DMSO—d$_6$): 9.75(1H,d); 8.65(1H,s); 8.55(1H,d, J=6.7Hz); 7.65(1H,d, J=6.7Hz); 7.2(2H,m); 6.9(1H,s); 5.8(1H,m); 5.6(2H,d, J=55.0Hz); 5.4(2H,bd); 5.15 (1H,d); 3.4(2H,m).

EXAMPLE 23

Synthesis of
7-β-[(Z)-2-(2-aminothiazol-4-yl)-2-fluoromethoxyiminoacetamido]-3-[2(1H,3H)-oxo-imidazo[4,5-b]-pyridiniummethyl]-3-cephem-4-carboxylate To a suspension of 300 mg of 7-β-[(Z)-2-(2-aminothiazol-4-yl)-2-fluoromethoxyiminoacetamido]-3-acetoxymethyl-3-cephem-4-carboxylic acid in 10 ml of dry dichloromethane was added, in one portion, 0.55 ml of N-methyl-N-(trimethylsilyl)trifluoroacetamide at room temperature. The reaction mixture was stirred for 5 minutes at 25° C. under a nitrogen atmosphere. To the stirred solution was added by pipette 0.33 ml of iodotrimethylsilane at 0° C., and the reaction mixture was then stirred at room temperature for 30 minutes. Thereafter, the solvent was evaporated off under reduced pressure to give an oil. The oil was dissolved in a mixture of 15 ml of acetonitrile and 0.3 ml of tetrahydrofuran, and the solution was stirred for 5 minutes. The stirred solution was added, in one portion, to a solution of 100 mg of 2(1H,3H)-oxo-imidazo[4,5-b]pyridine silylated with 0.90 ml of N,O-bis(trimethylsilyl)acetamide in 3 ml of acetonitrile. The reaction mixture was stirred for 3 hours at 25° C. and then added to a mixture of 0.5 ml of methanol and 2 ml of acetonitrile at 0° C. The mixture was stirred at 0° C. for 30 minutes. The precipitated solids were collected by filtration to give a solid product. 10 Ml of water was added to the solid, and the mixture was neutralized with a saturated sodium bicarbonate solution and then concentrated. The residue was purified by chromatography over silica gel to give 20 mg of the title compound.

m.p.: 231° C. (decomp.)

IR (KBr, cm$^{-1}$): 1616; 1668; 1767.

NMR (D$_2$O): 3.40(2H,q); 4.60(2H,q); 5.25(1H,d, J=4.80Hz); 5.85(2H,d, J=55.0Hz); 5.95(1H,d, J=4.80Hz); 7.10(1H,m); 7.15(1H,s); 7.50 (1H,d); 7.75(1H,d).

EXAMPLE 24

Synthesis of
7-β-[(Z)-2-(2-aminothiazol-4-yl)-2-carboxymethoxyiminoacetamido]-3-[2(1H,3H)-oxo-imidazo4,5-c]-pyridiniummethyl]-3-cephem-4-carboxylate To a suspension of 700 mg of 7-β-[(Z)-2-(2-aminothiazol-4-yl)-2-carboxymethoxyiminoacetamido]-3-acetoxymethyl-3-cephem-4-carboxylic acid in 15 ml of dry dichloromethane was added, in one portion, 0.95 ml of N-methyl-N-(trimethylsilyl)trifluoroacetamide at room temperature. The reaction mixture was stirred for 5 minutes at 25° C. under a nitrogen atmosphere. To the stirred solution was added by pipette 0.40 ml of iodotrimethylsilane at 0° C., and the reaction mixture was then stirred at room temperature for 30 minutes. Thereafter, the solvent was eva ported off under reduced pressure to give an oil. The oil was dissolved in a mixture of 10 ml of acetonitrile and 1.0 ml of tetrahydrofuran, and the solution was stirred for 5 minutes. The stirred solution was added, in one portion, to a solution of 180 mg of 2(1H,3H)-oxo-imidazo[4,5-c]pyridine silylated with 0.80 ml of N,O-bis(trimethylsilyl)acetamide in 10 ml of acetonitrile. The reaction mixture was stirred for 3 hours at 25° C. and then added to a mixture of 1.0 ml of methanol and 2 ml of acetonitrile at 0° C. The mixture was stirred at 0° C. for 30 minutes. The precipitated solids were collected by filtration to give a solid product. 10 Ml of water was added to the solid, and the mixture was neutralized with a saturated sodium bicarbonate solution and then concentrated. The residue was purified by chromatography over silica gel to give 80 mg of the title compound.

m.p.: 228° C. (decomp.)

IR (KBr, cm$^{-1}$): 1761; 1653; 1616.

NMR (DMSO—d$_6$): 3.35(1H,q); 4.50(2H,s); 4.75(2H,q); 5.25 (1H,d, J=4.7Hz); 5.85(1H,d, J=4.7Hz); 6.95(1H,s); 7.45(1H,d, J=6.7Hz); 8.35 (1H,d, J=6.7Hz); 8.60 (1H,s).

The title compounds illustrated in the above Examples are summarized in Table 1 below.

TABLE 1

| Example No. | n | R$_1$ | R$_2$ | R$_3$ | Fused position |
|---|---|---|---|---|---|
| Ex. 1 | 2 | CH$_3$— | H | H | 3,4-fused |
| Ex. 2 | 2 | CH$_3$CH$_2$— | H | H | 3,4-fused |
| Ex. 3 | 2 | HC≡C—CH$_2$— | H | H | 3,4-fused |
| Ex. 4 | 2 | 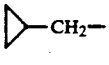 | H | H | 3,4-fused |
| Ex. 5 | 2 | HOOCCH$_2$— | H | H | 3,4-fused |
| Ex. 6 | 2 | 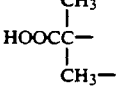 | H | H | 3,4-fused |

TABLE 1-continued

| Example No. | n | $R_1$ | $R_2$ | $R_3$ | Fused position |
|---|---|---|---|---|---|
| Ex. 7 | 2 | $CH_3-$ | $CH_3-$ | H | 3,4-fused |
| Ex. 8 | 2 | $CH_3-$ | $CH_3CH_2-$ | H | 3,4-fused |
| Ex. 9 | 2 | $CH_3-$ | $\triangleright-$ | H | 3,4-fused |
| Ex. 10 | 2 | $HOOCC(CH_3)_2-$ | $CH_3-$ | H | 3,4-fused |
| Ex. 11 | 2 | $HOOCC(CH_3)_2-$ | $CH_3CH_2-$ | H | 3,4-fused |
| Ex. 12 | 2 | $HOOCC(CH_3)_2-$ | $\triangleright-$ | H | 3,4-fused |
| Ex. 13 | 2 | $CH_3-$ | H | $CH_3-$ | 3,4-fused |
| Ex. 14 | 2 | $FCH_2-$ | H | H | 3,4-fused |
| Ex. 15 | 1 | $CH_3-$ | H | H | 3,4-fused |
| Ex. 16 | 1 | $CH_3-$ | $CH_3-$ | H | 3,4-fused |
| Ex. 17 | 1 | $CH_3-$ | $H_2N-$ | H | 3,4-fused |
| Ex. 18 | 1 | $CH_3-$ | $HOCH_2CH_2-$ | H | 3,4-fused |
| Ex. 19 | 1 | $CH_3-$ | H | H | 2,3-fused |
| Ex. 20 | 1 | $FCH_2-$ | H | H | 3,4-fused |
| Ex. 21 | 1 | $FCH_2-$ | $CH_3-$ | H | 3,4-fused |
| Ex. 22 | 1 | $FCH_2-$ | $H_2N-$ | H | 3,4-fused |
| Ex. 23 | 1 | $FCH_2-$ | H | H | 2,3-fused |
| Ex. 24 | 1 | $HOOCCH_2-$ | H | H | 3,4-fused |

INDUSTRIAL APPLICABILITY

The advantageous effects accruing from and the industrial applicability of the present invention are illustrated by means of the following experimental examples.

EXPERIMENTAL EXAMPLE 1 in vitro ACTIVITY

The in vitro antibacterial activities of several representative compounds of the present invention against various gram-positive and gram-negative microorganisms were evaluated by the following two-fold dilution method. As reference compounds, cefotaxime (CTX) and ceftazidime (CAZ) were employed.

Two-fold serial dilutions of the compounds of Examples 1, 2, 3, 5, 6, 7, 9 and 10, and the reference compounds were prepared. 1 .5 Ml of each dilution and subsequently 13.5 ml of Mueller-Hinton agar were added into a test tube and then mixed together. After thoroughly mixing, the mixture was poured into a sterilized Petri dish and coagulated. Each test microorganism-diluted suspension (about $10^4$ cfu/spot) was inoculated to the Mueller Hinton agar with an inoculator. After incubation at 37° C. for 18 hours, the minimum inhibitory concentrations (MICs: μg/ml) of the test and the reference compounds were measured. The results are shown in Table 2 below.

TABLE 2

| Strain | | Ex. 1 | Ex. 2 | Ex. 3 | Ex. 5 | Ex. 6 | Ex. 7 | Ex. 9 | Ex. 10 | CTX | CAZ |
|---|---|---|---|---|---|---|---|---|---|---|---|
| S.pyogenes | A8668 | 0.013 | 0.013 | 0.013 | 0.196 | 0.782 | 0.025 | 0.049 | 0.782 | 0.013 | 0.196 |
| S.aureus | A29213 | 1.563 | 1.563 | 0.782 | 25 | 12.5 | 1.563 | 3.125 | 12.5 | 0.782 | 12.5 |
| S.epidermidis | A12228 | 0.391 | 0.391 | 0.391 | 1.563 | 3.125 | 0.391 | 1.563 | 3.125 | 0.391 | 6.25 |
| E.coli | A10536 | 0.007 | 0.013 | 0.013 | 0.002 | 0.007 | 0.007 | 0.025 | 0.007 | 0.013 | 0.098 |
| P.mirabilis | A25933 | 0.013 | 0.025 | 0.013 | <0.002 | 0.007 | 0.007 | 0.049 | 0.013 | 0.013 | 0.049 |
| S.marcescens | A27117 | 0.025 | 0.049 | 0.049 | 0.004 | 0.007 | 0.007 | 0.782 | 0.013 | 0.049 | 0.391 |
| P.aeruginosa | A10145 | 3.125 | 6.25 | 3.125 | 1.563 | 1.563 | 12.5 | 25 | 6.25 | 25 | 3.125 |

EXPERIMENTAL EXAMPLE 2 in vitro ACTIVITY

In order to further illustrate the in vitro antibacterial activities of other representative compounds of the present invention, the minimal inhibitory concentrations (MIC) thereof against various gram-positive and gram-negative microorganisms were determined, and compared with those of cefotaxime (CTX) and ceftazidime (CAZ). The in vitro anti-bacterial activities were determined by the two-fold dilution method similar to that described in Experimental Example 1.

The two-fold serial dilutions of the test compounds and reference compounds were made and dispersed in Muller-Hinton agar medium. Then, 2 μl of standard test strain which had $10^4$/spot was inoculated on the medium, and was incubated at 37° C. for 20 hours. After the incubation, MICs μg/ml) of the test and reference compounds were measured. The results are shown in Table 3 below.

TABLE 3

| Strain | | Compound of | | | | | | | | | | |
|---|---|---|---|---|---|---|---|---|---|---|---|---|
| | | Ex. 15 | Ex. 20 | Ex. 24 | Ex. 16 | Ex. 21 | Ex. 17 | Ex. 22 | Ex. 19 | Ex. 23 | CTX | CAZ |
| S.pyogenes | A8668 | 0.007 | 0.007 | 0.098 | 0.013 | 0.007 | 0.007 | 0.013 | 0.007 | 0.013 | 0.007 | 0.098 |
| S.pyogenes | C4003 | 0.007 | 0.007 | 0.196 | 0.013 | 0.007 | 0.013 | 0.025 | 0.007 | 0.013 | 0.007 | 0.196 |
| S.aureus | A29213 | 1.563 | 0.782 | 12.5 | 1.563 | 1.563 | 1.563 | 1.563 | 0.782 | 0.782 | 0.782 | 6.25 |
| S.aureus | C4036 | 0.782 | 0.782 | 12.5 | 1.563 | 0.782 | 1.563 | 1.563 | 0.782 | 0.782 | 0.782 | 6.25 |
| MRSA | C1060 | 25 | 25 | 50 | 100 | 25 | 100 | 50 | 25 | 25 | 100 | 100 |
| S.epidermidis | A12228 | 0.391 | 0.391 | 6.25 | 0.391 | 0.391 | 0.391 | 0.782 | 0.391 | 0.391 | 0.391 | 3.125 |
| E.coli | A10536 | 0.004 | ≦0.002 | 0.025 | 0.007 | 0.004 | 0.007 | 0.007 | 0.025 | 0.025 | 0.013 | 0.049 |
| E.coli | A25922 | 0.013 | 0.007 | 0.049 | 0.013 | 0.013 | 0.013 | 0.025 | 0.098 | 0.098 | 0.049 | 0.196 |
| E.coli | C4052 | 0.007 | 0.004 | 0.025 | 0.007 | 0.007 | 0.007 | 0.013 | 0.049 | 0.025 | 0.013 | 0.098 |
| E.cloacae | C4008 | 0.004 | ≦0.002 | 0.013 | 0.004 | 0.004 | 0.004 | 0.007 | 0.013 | 0.013 | 0.007 | 0.025 |
| E.cloacae | C4009 | 0.013 | 0.007 | 0.013 | 0.013 | 0.007 | 0.013 | 0.013 | 0.098 | 0.049 | 0.049 | 0.098 |
| K.oxytoca | C4022 | 1.563 | 0.782 | 0.782 | 0.782 | 0.391 | 1.563 | 1.563 | 50 | 12.5 | 0.782 | 0.782 |
| K.pneumoniae | A10031 | 0.007 | 0.004 | 0.025 | 0.007 | 0.004 | 0.007 | 0.007 | 0.013 | 0.007 | 0.004 | 0.098 |
| K.pneumoniae | C4021 | 0.007 | 0.004 | 0.025 | 0.007 | 0.004 | 0.007 | 0.013 | 0.013 | 0.013 | 0.004 | 0.049 |
| P.mirabilis | A25933 | 0.013 | 0.004 | 0.007 | 0.013 | 0.007 | 0.013 | 0.013 | 0.007 | 0.007 | 0.013 | 0.049 |
| P.rettgeri | A9919 | 0.004 | 0.004 | 0.007 | 0.004 | 0.004 | 0.007 | 0.013 | 0.004 | 0.007 | 0.004 | 0.025 |
| S.typhimurium | C4045 | 0.013 | 0.007 | 0.049 | 0.013 | 0.007 | 0.013 | 0.013 | 0.049 | 0.025 | 0.013 | 0.196 |
| S.marcescens | A27117 | 0.013 | 0.007 | 0.025 | 0.013 | 0.007 | 0.013 | 0.013 | 0.049 | 0.049 | 0.049 | 0.098 |
| P.aeruginosa | A10145 | 1.563 | 1.563 | 3.125 | 3.125 | 1.563 | 3.125 | 3.125 | 25 | 12.5 | 25 | 3.125 |
| P.aeruginosa | C4028 | 0.004 | ≦0.002 | 0.007 | 0.007 | 0.004 | 0.007 | 0.007 | 0.004 | 0.007 | ≦0.002 | 0.013 |
| P.aeruginosa | A27853 | 0.782 | 0.782 | 1.563 | 1.563 | 0.782 | 1.563 | 1.563 | 12.5 | 6.25 | 12.5 | 1.563 |

What is claimed is:

1. A compound of the formula:

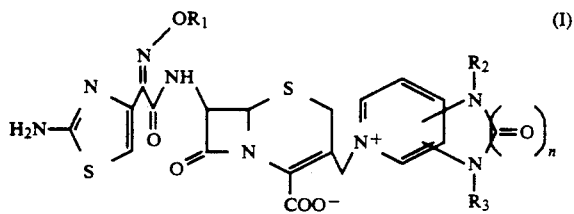

(I)

wherein

R$_1$ is hydrogen, or a lower alkyl, C$_3$–C$_4$ alkenyl, C$_3$–C$_4$ alkynyl or cycloalkylalkyl group, a fluoro-substituted lower alkyl group represented by the formula: —(CH$_2$)$_x$F in which x is an integer of 1 to 3, or a carboxy-substituted alkyl group represented by the formula:

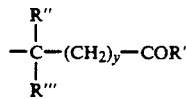

wherein

R' is a hydroxy, amino or C$_1$–C$_4$ alkoxy group; R'' and R''', which may be the same or different, represent hydrogen or a C$_1$–C$_3$ alkyl group, or R'' and R''' together with the carbon atom to which they are attached may form a C$_3$–C$_7$ carbocylic ring; and y is an integer of 0 to 3;

R$_2$ and R$_3$, which may be the same or different, represent hydrogen, or a lower alkyl, amino, carboxy-substituted lower alkyl, hydroxy-substituted lower alkyl or C$_3$–C$_7$ cycloalkyl group;

n is an integer of 1 or 2; and the 2-oxo-heterocyclic moiety is fused with the pyridine ring to form a 2,3- or 3,4-fused ring substituent at 3-position of the cephem nucleus; or a pharmaceutically acceptable salt, physiologically hydrolyzable ester or solvate thereof.

2. The compound of claim 1, wherein R$_1$ is a methyl, ethyl, cyclopropylmethyl, fluoromethyl, 2-carboxyprop-2-yl or carboxymethyl group; R$_2$ is hydrogen, or a methyl, ethyl, cyclopropyl, amino or hydroxyethyl group; and R$_3$ is hydrogen or a methyl group.

3. The compound of claim 1, which is

7-β-[(Z)-2-(2-aminothiazol-4-yl)-2-methoxyiminoacetamido]-3-[2,3-(1H,4H)-dioxo-pyrazino[5,6-c]pyridiniummethyl]-3-cephem-4-carboxylate;

7-β-[(Z)-2-(2-aminothiazol-4-yl)-2-ethoxyiminoacetamido]-3-[2,3(1H,4H)-dioxo-pyrazino[5,6-c]pyridiniummethyl]-3-cephem-4-carboxylate;

7-β-[(Z)-2-aminothiazol-4-yl)-2-propynyloxyiminoacetamido]- 3-[2,3(1H,4H)-dioxopyrazino[5,6-c]pyridiniummethyl]-3-cephem-4-carboxylate;

7-β-[(Z)-2-(2-aminothiazol-4-yl)-2-cyclopropylmethoxyimino-acetamido]-3-[2,3(1H,4H)-dioxopyrazino[5,6-c]pyridiniummethyl]-3-cephem 4-carboxylate;

7-β-[(Z)-2-(2-aminothiazol-4-yl)-2-carboxymethoxyiminoacetamido]-3-[2,3(1H,4H)-dioxo-pyrazino[5,6-c]pyridiniummethyl]-3-cephem-4-carboxylate;

7-β-[(Z)-2-(2-aminothiazol-4-yl)-2-(2-carboxyprop-2-yl)-oxyiminoacetamido]-3-[2,3(1H,4H)-dioxopyrazino[5,6-c]-pyridiniummethyl]-3-cephem-4-carboxylate;

7-β-[(Z)-2-(2-aminothiazol-4-yl)-2-methoxyiminoacetamido]-3-[1-methyl-2,3(4H)-dioxopyrazino[5,6-c]pyridiniummethyl]- 3-cephem-4-carboxylate;

7-β-[(Z)-2-(2-aminothiazol-4-yl)-2-methoxyiminoacetamido]-3-[1-ethyl-2,3(4H)-dioxopyrazino[5,6-c]pyridimiummethyl]-3-cephem-4-carboxylate;

7-β-[(Z)-2-(2-aminothiazol-4-yl)-2-methoxyiminoacetamido]-3-[1-cyclopropyl-2,3(4H)-dioxopyrazino[5,6-c]pyridiniummethyl]-3-cephem-4-carboxylate;

7-β-[(Z)-2-(2-aminothiazol-4-yl)-2-(2-carboxyprop-2-yl)oxyiminoacetamido]-3-[1-methyl-2,3(4H)-dioxopyrazino[5,6-c]-pyridiniummethyl]-3-cephem-4-carboxylate;

7-β-[(Z)-2-(2-aminothiazol-4-yl)-2-(2-carboxyprop-2-yl)oxyiminoacetamido]-3-[1-ethyl-2,3(4H)-dioxopyrazino[5,6-c]-pyridiniummethyl]-3-cephem-4-carboxylate;

7-β-[(Z)-2-(2-aminothiazol-4-yl)-2-(2-carboxyprop-2-yl)oxyiminoacetamido]-3-[1-cyclopropyl-2,3(4H)-dioxo-pyrazino-[5,6-c]pyridiniummethyl]-3-cephem-4-carboxylate;

7-β-[(Z)-2-(2-aminothiazol-4-yl]-2-methoxyiminoacetamido]-3-[4-methyl-2,3(1H)-dioxo-pyrazino[5,6-c]pyridiniummethyl]-3-cephem-4-carboxylate;

7-β-[(Z)-2-(aminothiazol-4-yl)-2-fluoromethoxyiminoacetamido]-3-[2,3(1H,4H)-dioxo-pyrazino[5,6-c]pyridiniummethyl]-3-cephem-4-carboxylate;

7-β-[(Z)-2-(2-aminothiazol-4-yl)-2-methoxyiminoacetamido]-3-[2(1H,3H)-oxo-imidazo[4,5-c]pyridiniummethyl]-3-cephem-4-carboxylate;

7-β-[(Z)-2-(2-aminothiazol-4-yl)-2-methoxyiminoacetamido]-3-[1-methyl-2(3H)-oxo-imidazo[4,5-c]pyridiniummethyl]-3-cephem-4-carboxylate;

7-β-[(Z)-2-(2-aminothiazol-4-yl)-2-methoxyiminoacetamido]-3-[1-amino-2(3H)-oxo-imidazo[4,5-c]pyridiniummethyl]-3-cephem-4-carboxylate;

7-[1-(2-hydroxyethyl)-2(3H)-oxo-imidazo[4,5-c]pyridinium-3-[1-(2-hydroxyethyl)-2(3H)-oxo-imidazo[4,5-c]pyridiniummethyl]-3-cephem-4-carboxylate;

7-β-[(Z)-2-(2-aminothiazol-4-yl)-2-methoxyiminoacetamido]-3-[2(1H,3H)-oxo-imidazo[4,5-b]pyridiniummethyl]-3-cephem-4-carboxylate;

7-β-[(Z)-2-(2-aminothiazol-4-yl)-2-fluoromethoxyiminoacetamido]-3-[2(1H,3H)-oxo-imidazo[4,5-c]pyridiniummethyl]-3-cephem-4-carboxylate;

7-β-[(Z)-2-(2-aminothiazol-4-yl)-2-fluoromethoxyiminoacetamido]-3-[1-methyl-2(3H)-oxo-imidazo[4,5-c]pyridiniummethyl]-3-cephem-4-carboxylate;

7-β-[(Z)-2-(2-aminothiazol-4-yl)-2-fluoromethoxyiminoacetamido]-3-[1-amino-2(3H)-oxo-imidazo[4,5-c]pyridiniummethyl]-3-cephem-4-carboxylate;

7-β-[(Z)-2-(2-aminothiazol-4-yl)-2-fluoromethoxyiminoacetamido]-3-[2(1H,3H)-oxo-imidazo[4,5-b]pyridiniummethyl]-3-cephem-4-carboxylate; or 7-β-[(Z)-2-(2-aminothiazol-4-yl)-2-carboxymethoxyiminoacetamido]-3-[2(1H,3H)-oxo-imidazo[4,5-c]pyridiniummethyl]-3-cephem-4-carboxylate.

4. A pharmaceutical composition which comprises a therapeutically effective amount of one or more of the cephalosporin compounds of the formula (I) according any of claims 1 to 3, or a pharmaceutically acceptable salt, physiologically hydrolyzable ester or slovate thereof, in association with a pharmaceutically acceptable carrier, excipient, or other additives therefor.

5. A method of treating bacterial infection comprising administering to a host on effective amount of at least one compound according to claim 1.

6. A method of treating bacterial infection comprising administering to a host on effective amount of at least one compound according to claim 2.

7. A method of treating bacterial infection comprising administering to a host on effective amount of at least one compound according to claim 3.

8. The method of claim 5, wherein the bacterial infection is caused by a gram-negative bacteria.

9. The method of claim 6, wherein the bacterial infection is caused by a gram-negative bacteria.

10. The method of claim 7, wherein the bacterial infection is caused by a gram-negative bacteria.

* * * * *